United States Patent [19]

Hofstein

[11] 4,276,887
[45] Jul. 7, 1981

[54] FOOT EXERCISER

[75] Inventor: Steven R. Hofstein, North Brunswick, N.J.

[73] Assignee: World Medical Marketing Corporation, New York, N.Y.

[21] Appl. No.: 111,531

[22] Filed: Jan. 14, 1980

Related U.S. Application Data

[62] Division of Ser. No. 85,330, Oct. 29, 1979.

[51] Int. Cl.³ .............................................. A61B 5/02
[52] U.S. Cl. .................................. 128/691; 128/25 B; 272/96; 272/DIG. 6
[58] Field of Search .................... 128/25 R, 25 B, 46, 128/26, 707, 691, 693–694; 272/73, 96, DIG. 6

[56] References Cited

U.S. PATENT DOCUMENTS 3,395,698   8/1968   Morehouse ......................... 128/707

Primary Examiner—Robert W. Michell
Assistant Examiner—Francis J. Jaworski
Attorney, Agent, or Firm—Ostrolenk, Faber, Gerb & Soffen

[57] ABSTRACT

A foot exercising device is disclosed. The foot exercising device includes a pair of foot pedals and a motor for reciprocating the foot pedals. A slip clutch is connected between the foot pedals and the motor to enable the foot pedals to be reciprocated independently of the motor. In the preferred embodiment, a control circuit controls the operation of the motor as a function of the number of reciprocations of the foot pedals and/or as a function of the blood flow through the patient using the foot exercising device.

3 Claims, 10 Drawing Figures

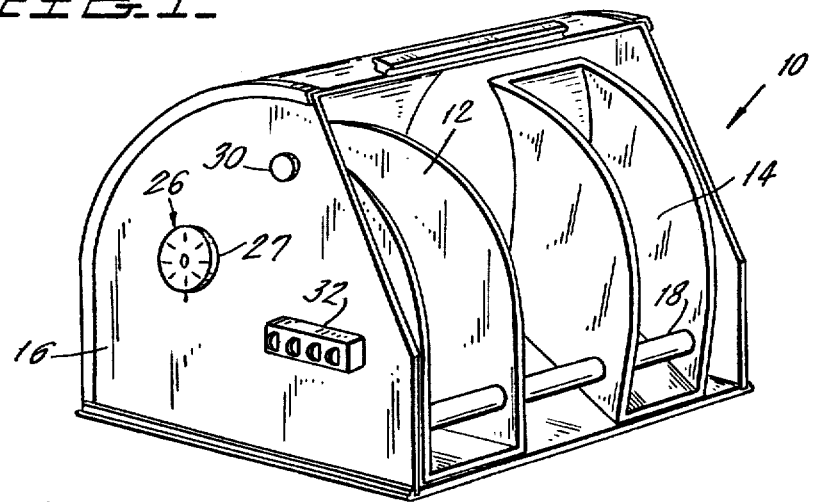
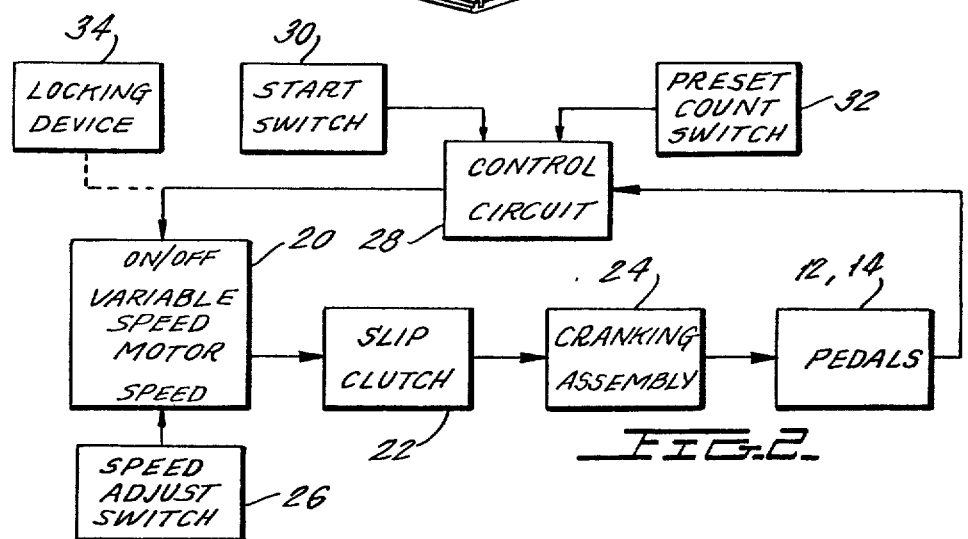
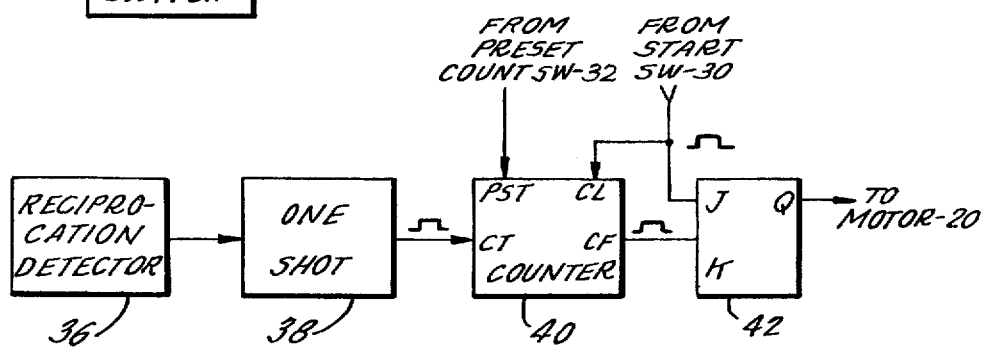

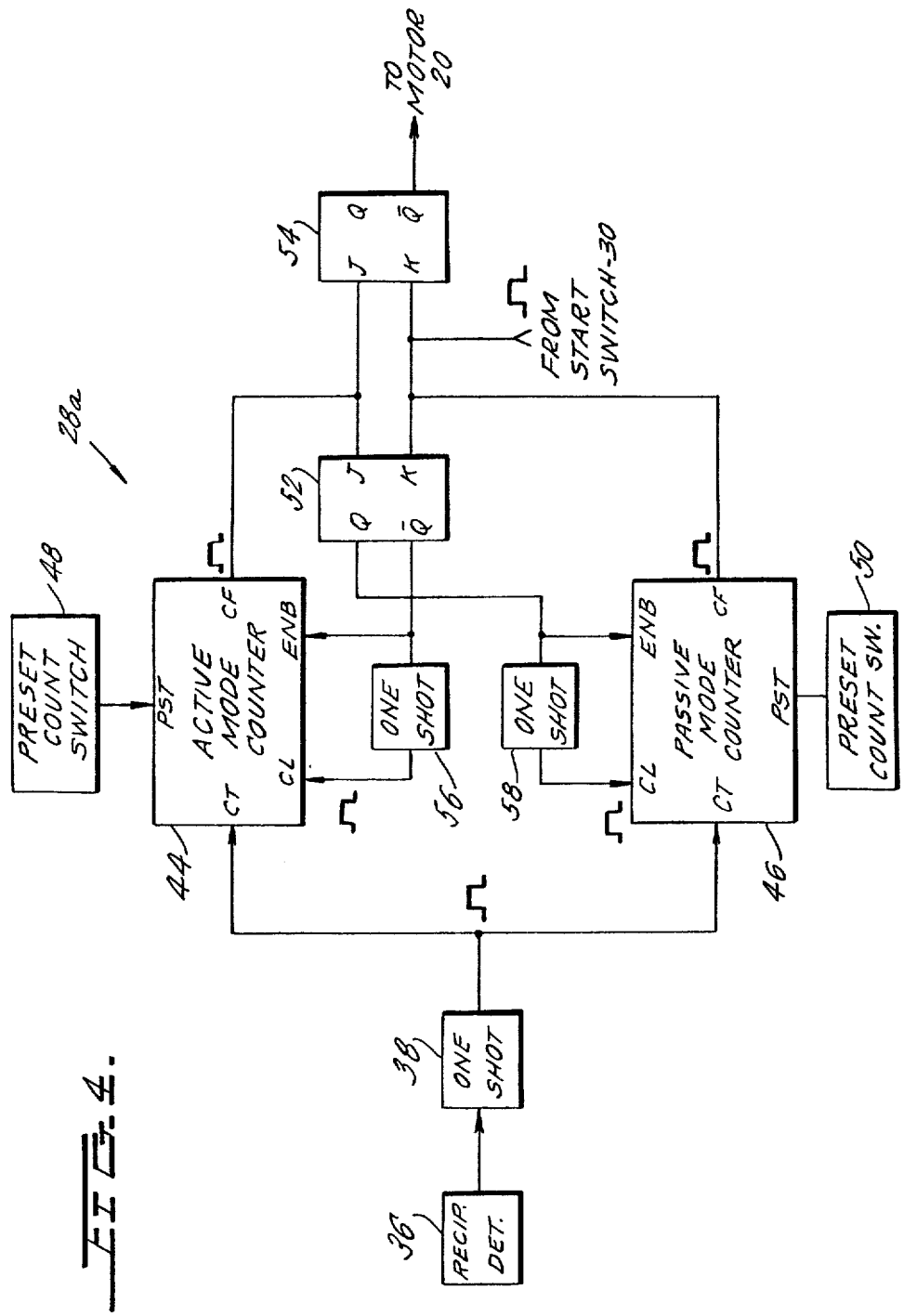

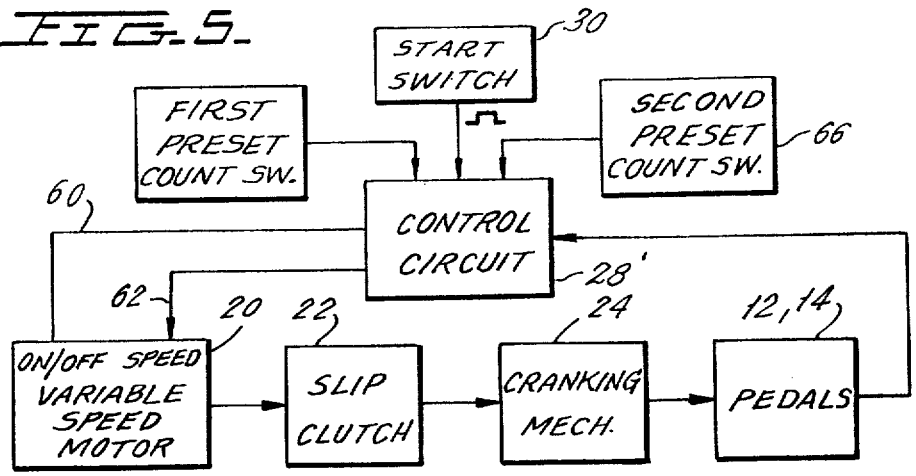
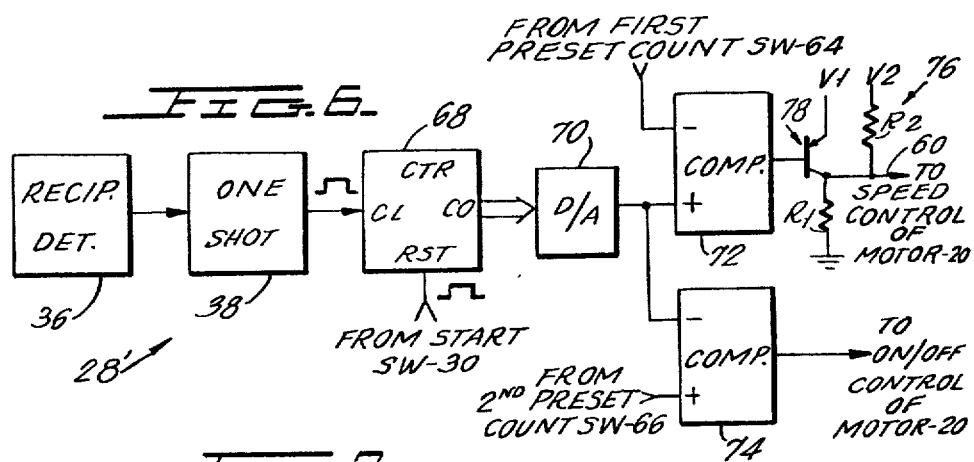
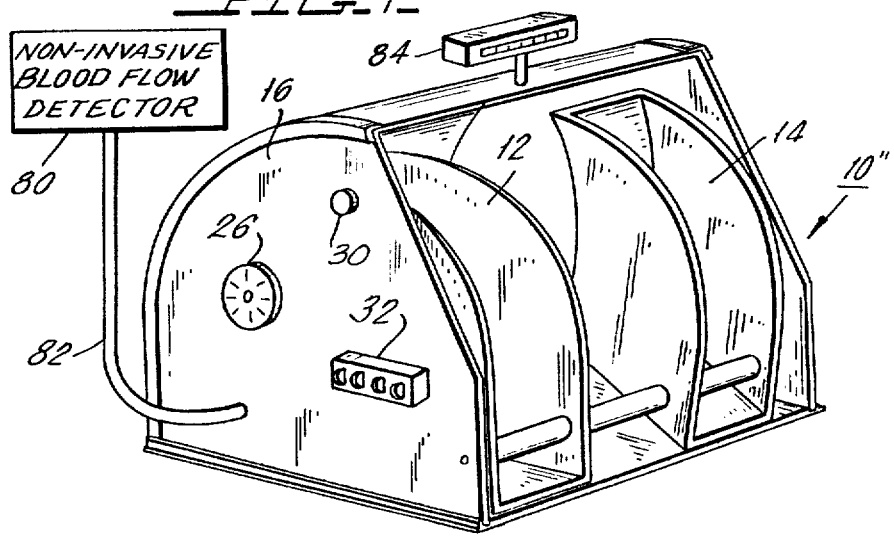

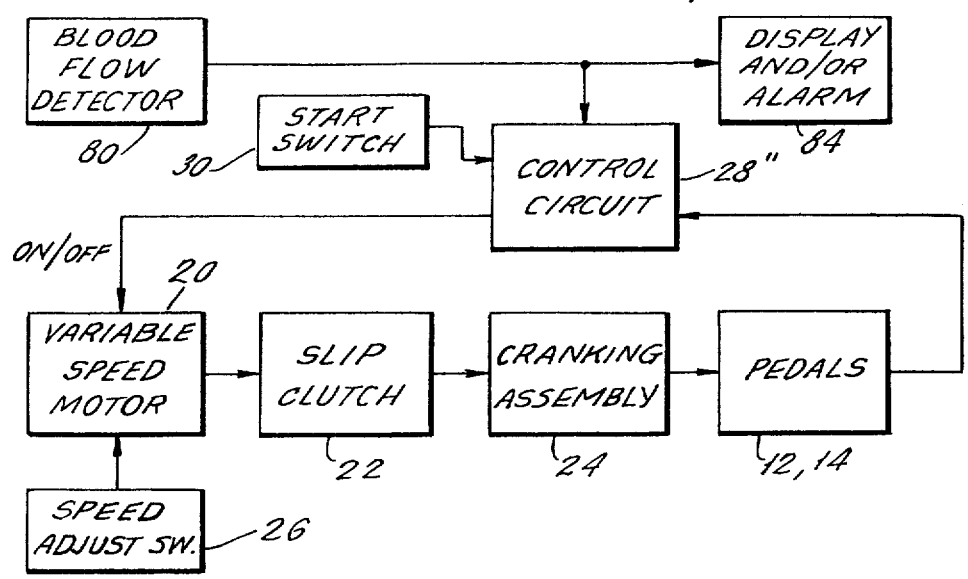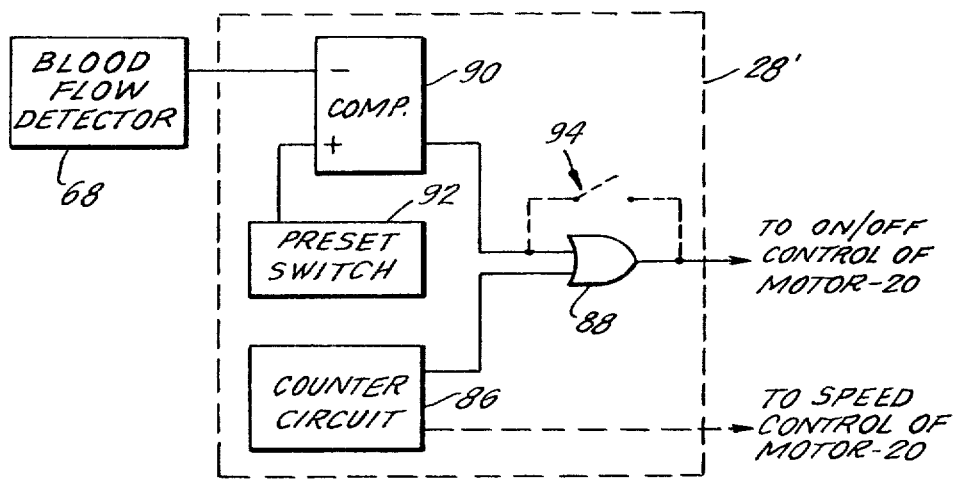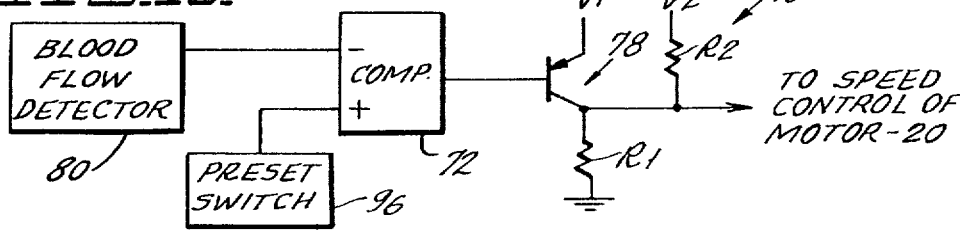

FOOT EXERCISER

RELATED APPLICATIONS

This is a divisional of U.S. Pat. application Ser. No. 85,330, filed Oct. 29, 1979.

BACKGROUND OF THE INVENTION

The present invention is directed towards a foot exercising device, and more particularly to a foot exercising device which is useful in the prevention of thrombosis of the legs. Devices of this general nature are known in the prior art and are exemplified by U.S. Pat. Nos. 3,526,220 and 3,917,261.

Each year nearly 100,000 hospital patients die of pulmonary embolisms. These potentially lethal clots usually form in the leg veins and are often caused by stagnation of blood circulation while the patient is immobile following surgery or illness.

Measures have been employed to prevent venous clotting in the legs including anti-coagulants, compression bandages, elastic stockings, leg elevation and early ambulation. For a variety of reasons, none of these has proved to be satisfactorily effective. Patients exhibit a wide range of susceptibility to a standard anti-coagulant dose, which makes adequate prophylactic contrl difficult. Compression bandages and elastic stockings rarely maintain the necessary uniform compression on the leg veins. Continued leg elevation is difficult to maintain for long periods and imposes an additional load on the cardiovascular system which many patients cannot tolerate. Ambulation often amounts to no more than a few steps around the bed once or twice a day.

There is persuasive clinical evidence that the best method for preventing thromboembolism is to increase the speed of the blood flow in the deep veins of the lower leg. Short of full ambulation (impossible for many post-operative and seriously ill patients), this increase in venous flow velocity is best accomplished by a regimen of leg exercise carried out with adequate duration and frequency.

The purpose of leg exericising devices such as that described in the above-noted patents, as well as that described herein, is to automatically exercise the patient's legs so as to increase blood circulation in the area and thereby prevent the formation of thromboemboli. The prior art foot exercising devices have recognized that it is desirable to run the exercisers in both a passive and an active mode. In the passive mode of operation, the leg exercising device moves the patient's feet up and down through a predetermined arc for a preselected time period. In the active mode of operation, the patient supplies the foot power himself against the resistive pressure which is selected by means of a brake pressure control knob.

BRIEF DESCRIPTION OF THE INVENTION

While the foregoing prior art foot exercising devices have been generally successful, the present invention includes many features which result in improved patient care. As noted above, the prior art foot exercising devices operate in both a passive and an active mode. This is highly desirable since it enables the patient to strengthen his legs by reciprocating the pedals on his own during the active mode and, at the same time, ensures at least periodic movement of the patient's legs (during the passive mode of operation). The major drawback of the prior art devices is that the patient cannot pedal on his own during the passive mode of operation. As such, the intervals during which the patient can exercise his legs on his own is limited to the intervals during which the device is in the active mode of operation.

To overcome this drawback, the present invention utilizes a slip clutch or similar apparatus which permits the patient to disengage the motor, and thereby pedal on his own, during the passive mode of operation by merely pedaling faster than the speed required by the motor. This same mechanism enables the patient to reciprocate the pedals on his own during the active mode of operation. As such, the present invention provies the patient with total freedom to exercise on his own whenever he finds it so desirable. At the same time, since the invention does operate in the passive mode of operation, the physician can be assured that the patient's legs will receive at least a minimal amount of movement.

In the above-noted prior art foot exercisers, the time duration during the passive and active modes of operation was controlled by a presettable timer. In the present invention, the active and passive modes are not defined by preset time periods but by the number of reciprocations of the pedals of the device. To this end, counters are provided to count the pedal reciprocations during both the active and passive modes of operation and to switch the device between these modes as a function thereof.

Yet another feature of the invention is the inclusion of control circuitry which varies the reciprocation frequency of the pedals of the foot exerciser during the passive mode of operation as a function of the number of pedal reciprocations during the passive mode.

Yet another major feature of the present invention is the use of a non-invasive blood flow detector which generates an output signal indicative of the instantaneous blood flow through the patient's legs. This signal may be used to provide a visual display of the blood flow and/or to generate an alarm signal whenever the blood flow falls below a predetermined value. Finally, this signal may be used either to vary the reciprocation frequency of the pedals during the passive mode or to automatically switch the foot exercising device into the passive mode whenever the blood flow through the legs of the patient falls below a predetermined value.

BRIEF DESCRIPTION OF THE DRAWINGS

For the purpose of illustrating the invention, there is shown in the drawings an embodiment which is presently preferred; it being understood, however, that the invention is not limited to the precise arrangements and instrumentalities shown.

FIG. 1 is a perspective view of a foot exercising device constructed in accordance with the principles of the present invention.

FIG. 2 is a block diagram of the foot exercising device of FIG. 1.

FIG. 3 is a first embodiment of the control circuit of FIG. 2.

FIG. 4 is a second embodiment of the control circuit of FIG. 2.

FIG. 5 is a block diagram of a second embodiment of a foot exercising device constructed in accordance with the principles of the present invention.

FIG. 6 is a block diagram of the control circuit of FIG. 5.

FIG. 7 is a perspective view of a third embodiment of a foot exercising device constructed in accordance with the principles of the present invention.

FIG. 8 is a block diagram of the embodiment of FIG. 7.

FIG. 9 is a block diagram of the control circuit of FIG. 8.

FIG. 10 is a block diagram of a possible modification of the control circuit of FIG. 8.

DETAILED DESCRIPTION OF THE PREFERRED EMBODIMENTS

Referring now to the drawings, wherein like numerals indicate like elements, there is shown in FIG. 1 a foot exercising device constructed in accordance with the principles of the present invention and designated generally as 10. A block diagram of the foot exercising device of FIG. 1 is illustrated in FIG. 2.

As best viewed in FIG. 1, foot exercising device 10 includes a pair of pedals 12, 14 which are pivotally connected to a housing 16 by an elongated shaft 18 extending between the opposite side walls of housing 16. Reciprocating motion is imparted to pedals 12, 14 by a motor 20 (preferably, but not necessarily, a variable speed motor) which is located in housing 16 and whose speed is determined by a speed adjust switch 26 which is coupled to housing 16. Speed adjust switch 26 may include a rotary knob 27 coupled to the outside of housing 16 and a variable resistor whose rotary shaft is coupled for rotation therewith. More generally, speed adjust switch 26 may be any switch which will generate an output signal (normally an analog signal) indicative of the desired speed of motor 20.

The output shaft (not shown) of motor 20 is coupled to pedals 12, 14 via a slip clutch 22 and a cranking assembly 24 which serves to reciprocate pedals 12, 14 about shaft 18 responsive to the rotary motion of the output shaft of motor 20. While any suitable cranking assembly may be used, one acceptable assembly is described in U.S. Pat. No. 3,917,261. Cranking assembly 24 is preferably adjustable so as to permit the pedals 12, 14 to be reciprocated out of phase with each other by any amount between 90° and 180°. It has been found that by adjusting the phase of pedals 12, 14 to an intermediate setting of, for example, 120°, the patient experiences a more pleasant sensation when using the device 10.

The use of slip clutch 22 enables the patient to override the driving force of motor 20 whenever he has sufficient energy to do so. This is an extremely desirable feature since it permits the physician to ensure that the patient's legs will automatically be exercised and at the same time permits the patient to strengthen his legs by overriding the motor and reciprocating pedals 12, 14 on his own. By way of example, the physician may adjust the speed of variable speed motor 20 to run at a relatively slow speed which causes pedals 12, 14 to reciprocate at, for example, 20 reciprocations per minute. The physician will then instruct the patient to pedal on his own whenever he possesses sufficient strength to do so. The patient will do this by merely reciprocating pedals 12, 14 at a reciprocation rate of greater than 20 reciprocations per minute. In this connection, it should be noted that slip clutch 22 will preferably slip only in one direction such that cranking assembly 24 disengages from the output shaft (not shown) of motor 20 only when pedals 12, 14 are reciprocated at a faster speed than that required by motor 20.

While the speed of variable speed motor 20 is controlled by speed adjust switch 26, the on-off state of motor 20 is controlled by control circuit 28. More particularly, control circuit 28 turns on motor 20 responsive to receipt of a start signal from a start switch 30 (or other appropriate initiating mechanism) and maintains motor 20 in the on condition until the pedals 12, 14 have reciprocated a preset number of times determined by preset count switch 32. As best seen in FIG. 1, preset count switch 32 is preferably coupled to the outside of housing 16 and can take the form of a plurality of thumb wheel switches which generate a digital output signal indicative of the desired number of reciprocations during the passive mode of operation. This number may be adjusted by the physician or the patient by merely rotating the thumb wheel switches. While thumb wheel switches are illustrated, any appropriate switch mechanism which can generate an output signal indicative of the desired number of reciprocations during the passive mode of operation may be used. After pedals 12, 14 have been reciprocated the preset number of times, control circuit 28 turns off motor 20.

In the event that the patient does not override motor 20 by pedaling faster than the speed set by speed adjust switch 26, control circuit 28 maintains foot exercising device 10 in the passive mode of operation for a time period determined by the speed of motor 20 and the preset count. If, however, the patient overrides the motor 20 by pedaling faster than the speed required by motor 20, the time duration during which foot exercising device 10 remains in the passive mode will vary independently of the speed of motor 20 and the preset count. In either case, control circuit 28 turns motor 20 off after pedals 12, 14 have been reciprocated the predetermined number of times. When motor 20 is off, foot exercising device 10 is in an active mode wherein the patient may reciprocate pedals 12, 14 on his own since slip clutch 22 permits pedals 12, 14 to be reciprocated independently of motor 20. As such, foot exercising device 10 switches between a single passive and a single active mode of operation.

It is sometimes desirable to ensure that the patient does not pedal the foot exercising device subsequent to the passive mode of operation. In such a case, a locking device 34 is added to the foot exercising device 10. Locking device 34 is enabled by control circuit 28 whenever control circuit 28 shuts off motor 20 and prevents pedals 12, 14 from reciprocating. By way of example, locking device 34 may be a friction brake which presses against pedals 12, 14 whenever motor 20 if off. Whenever the locking device 34 has been added to the foot exercising device 10, device 10 operates only in a passive mode. The passive mode may, however, be overridden by the patient as a result of the presence of slip clutch 22.

One suitable control circuit 28 for the embodiment of FIG. 2 is illustrated in FIG. 3. As shown therein, control circuit 32 includes a reciprocation detector 36, a one shot 38, a counter 40 and a J-K flip/flop 42. Reciprocation detector 36 monitors the movement of at least one of the pedals 12, 14 and generates an output signal whenever the monitored pedal completed one full reciprocation. By way of example, but not limitation, reciprocation detector 36 may be a microswitch located in housing 16 in such a position that the microswitch is closed whenever pedal 12 is in its lowermost position. Such a detection circuit will generate a single output signal for each reciprocation of pedals 12, 14.

The output of reciprocation detector 36 is applied to one shot 38 which generates a single pulse (hereinafter count pulse) of predetermined duration at its output responsive to each output signal generated by reciprocation detector 36. The count pulse generated by one shot 38 is applied to the count input CT of counter 40 and causes the count in counter 40 to increase by 1 each time a new count pulse is applied thereto. The count in counter 40 is initially set to 0 by the start pulse generated by start switch 30 (see FIG. 2). This signal is applied both to the clear input CL of count 40 and to the J input of J-K flip/flop 42. In addition to setting the count in counter 40 to zero, the start pulse generated by start switch 30 sets flip/flop 42 causing its Q output to go to the binary "1" level. The Q output of flip/flop 42 is applied to the on/off input of motor 20 which is turned on when the Q output of flip/flop 42 is at the binary "1" level.

Once foot exercising device 10 has been placed in the passive mode of operation by the start signal generated by start switch 30, counter 40 continues to count the count pulses generated by one shot 38 until the count in counter 40 reaches a preset count determined by the preset count switch 32 (see FIG. 2). The digital signal generated by switch 32 is applied to the preset input PST of counter 40. When the count in counter 40 reaches this preset level, it generates a single pulse on its count full output CF which is applied to the K input of flip/flop 42. This causes flip/flop 42 to reset thereby switching the Q output of flip/flop 42 to the binary "0" level. As a result, motor 20 is turned off whenever counter 40 has counted the predetermined number of reciprocations set by preset count switch 32.

A somewhat more sophisticated embodiment of control circuit 28 is illustrated in FIG. 4. To distinguish over the embodiment of FIG. 3, this circuit will be identified as control circuit 28a. As noted above, control circuit 28 causes foot exercising device 10 to be cycled through a single passive and a single active mode. In order to reinitiate a passive mode of operation, the start switch 30 must again be depressed. In contrast, control circuit 28a illustrated in FIG. 4 continually cycles foot exercising device 10 through several sequential passive and active modes of operation. The particular duration of each of these modes is determined as a function of a preset reciprocation count for the passive mode of operation and a second preset reciprocation count for the active mode of operation. Since the slip clutch 22 permits the patient to override the motor 20 in both the active and passive modes of operation, both of these modes are reciprocation dependent and time independent. As shown in FIG. 4, the counter 40 of the embodiment of FIG. 3 is replaced by separate passive mode and active mode counters 44, 46, respectively. Passive mode counter 44 counts the number of reciprocations of pedals 12, 14 during the passive mode of operation by counting the number of count pulses generated by one shot 38 during this mode. Active mode counter 48 counts the number of reciprocations of pedals 12, 14 during the active mode of operation by counting the number of count pulses generated during the active mode. The number of reciprocations required during the passive mode of operation is determined by a preset count switch 48. The number of reciprocations required during the active mode of operation is determined by a preset count switch 50. Switches 48, 50 replace the single preset count switch 32 of the foregoing embodiment. Accordingly, when utilizing the control circuit 28a of FIG. 4, the single preset count switch 32 illustrated in FIG. 1 is replaced by a pair of count switches. If desired, the two count switches could be replaced by a single push-button keyboard circuit and a pair of memories. The push-button keyboard circuit would be used to enter the desired active and passive mode counts in respective ones of the memories. The counts stored in each of the memories would be applied to respective preset inputs PST of memories 44, 46.

Transfer between the passive and active modes of operation is effectuated by J-K flip/flop 58 whose operation is controlled by the count full outputs CF of counters 44, 46. When foot exercising device 10 is first turned on, a start pulse is applied to the K input of J-K flip/flops 52, 54 by start switch 30. As a result, both flip/flops 52, 54 are reset causing their Q outputs to toggle to the binary "0" level and 52, 54 causing their $\overline{Q}$ outputs to toggle to the binary "1" level. The $\overline{Q}$ output of flip/flop 54 is applied to the on/off input of motor 20 and turns motor 20 on (thereby placing foot exercising device 10 in the passive mode). The binary "1" appearing at the $\overline{Q}$ output of flip/flop 52 is applied to the enable input ENB of passive mode counter 44 thereby enabling counter 44. The binary "1" appearing at the $\overline{Q}$ output of flip/flop 52 is also applied to a one shot 56 which generates a single pulse of predetermined duration each time the $\overline{Q}$ output of flip/flop 52 transitions to the binary "1" level. As such, whenever flip/flop 52 toggles to the reset state, the passive mode counter 44 is enabled, its counter reset to zero and the counter begins counting the count pulses generated by one shot 38. Simultaneously, active mode counter 46 is disabled since the Q output of flip/flop 52 is at the binary "0" level.

Once the count in counter 44 has reached the preset number determined by preset count switch 48, counter 44 generates a single pulse (an end of passive mode signal) on its count full output CF which is applied to the J input of flip/flops 52, 54. This action sets both flip/flops. As a result, the $\overline{Q}$ output of flip/flop 54 toggles to the binary "0" level, shutting off motor 20 and placing foot exercising device 10 in the active mode of operation. Simultaneously, the Q and $\overline{Q}$ outputs of flip/flop 52 toggle to the binary "1" and binary "0" levels, respectively, thereby clearing and enabling active mode counter 46, and disabling passive mode counter 44.

At this point, active mode counter 46 begins counting the count pulses generated by one shot 38 and continues counting these pulses until the count in counter 46 reaches the preset level determined by preset count switch 50. At this time, active mode counter 46 generates a single output pulse (an end of passive mode signal) at its count full output CF which is applied to the K input of flip/flops 52, 54. This action sets flip/flops 52, 54, thereby re-enabling motor 20 and passive mode counter 44, disabling passive mode counter 46, and repeating the above process.

In each of the foregoing embodiments of the invention, control circuits 28, 28a only control the on/off condition of motor 20. In the embodiment of the invention illustrated in FIG. 5, control circuit 28' controls the speed of motor 20 as well as the on/off condition thereof. In the embodiment described below, control circuit 28' operates motor 20 (and therefore pedals 12, 14) at either one of two discrete speeds as a function of the number of reciprocations of pedals 12, 14 during the passive mode of operation. It should be recognized, however, that the control circuit 28' can be used to adjust the speed of motor 20 in any desired manner. For example, control circuit 28' can be used to adjust the speed of variable speed motor 20 as a linear function of the number of reciprocations of pedals 12, 14.

In the preferred embodiment, the operation of foot exercising device 10 is initiated by depressing start switch 30 so as to generate a start pulse which is applied to control circuit 28'. In response to this pulse, control circuit 28' generates a signal on output line 60 which causes variable speed motor 20 to turn on. Simultaneously, control circuit 28' generates a signal on line 62 which sets the speed of motor 20 to a first value corresponding to a preset pedal reciprocation frequency, for example, 20 reciprocations per minute.

Control circuit 28' maintains this reciprocation frequency until it has detected a first predetermined number of pedal reciprocations, this number being determined by first preset count switch 64. At this time, control circuit 28' changes the signal on line 62 to cause motor 20 to operate at a second speed corresponding to a second pedal reciprocation frequency (e.g., 30 reciprocations per minute). Finally, after control circuit 28' detects a second, higher, number of pedal reciprocations, this number being determined by a second preset count switch 66, control circuit 28' changes the signal on line 60 so as to shut off variable speed motor 20 and place foot exercising device 10' in the active mode of operation.

One suitable control circuit 28' is illustrated in FIG. 6. As shown therein, control circuit 28' includes reciprocation detector 36, one shot 38, counter 68, digital-to-analog (hereinafter D/A) converter 70 and comparators 72, 74. As in the earlier embodiments, reciprocation detector 36 and one shot 38 combine to generate a single count pulse applied to the clock input CL of counter 68 responsive to each reciprocation of pedals 12, 14. Counter 68 continually counts these pulses and generates a binary signal on its count output CO indicative of the instantaneous count in counter 68. In addition to receiving the clock pulses generated by one shot 38, counter 68 receives the start pulse generated by start switch 30 such that the count in counter 68 is cleared at the beginning of each passive mode of foot exercising device 10'.

The count output CO of counter 68 is applied to D/A converter 70 which converts this signal to an analog signal and applies the converted signal to the inverting input terminal of comparators 72, 74. Comparator 72 compares the instantaneous count in counter 68 with the preset count determined by first preset count switch 64 and controls the operation of speed adjust circuit 76 as a function thereof. Speed adjust circuit 76 includes a transistor 78 and resistors R1 And R2 and applies either a first predetermined voltage or a second predetermined voltage to the speed control input of motor 20 as a function of the condition of transistor 78. Particularly, when transistor 78 is on, the voltage V1 appearing at its emitter is applied to the speed control input of motor 20 via line 60. When transistor 78 is off, a second voltage, determined by the magnitude of voltage V2 and the voltage divider R1-R2, is applied to the speed control input of motor 20 via line 60.

As long as the count in counter 68 remains below the predetermined count set by said preset count switch 64, the output of comparator 72 will be at the binary "0" level and transistor 78 will be turned on. In this condition, the voltage V1 will be applied to the speed control of motor 20. As soon as the count in counter 68 rises above the level determined by preset count switch 64, the output of comparator 72 will switch to the binary "1" level turning transistor 78 off. In this condition, the voltage applied to the speed control input of motor 20 will change to the value determined by voltage V2 and voltage divider R1-R2. If voltages V1 and V2 are kept constant, foot exercising device 10' will be capable of operating at only two discrete speeds. For this reason, it is usually desirable to provide means for varying the voltages V1, V2 so as to enable the physician to select the two desired motor speeds, and therefore the two pedal reciprocation frequencies, in accordance with the needs of the patient. A similar result may be obtained by replacing either resistor R1, R2 with an appropriate potentiometer.

As noted above, the output of D/A converter 70 is also applied to the inverting input terminal of comparator 74. Comparator 74 controls the on/off condition of motor 20. To this end, comparator 74 compares the count in counter 68 to the preset count determined by second preset count switch 66. As long as the count in counter 68 remains below this count, comparator 70 will generate a binary "1" on its output. This signal is applied to the on/off control input of motor 20 via line 62 and turns the motor 20 on. The output of comparator 74 remains at this level until the count in counter 68 reaches the preset level determined by second preset count switch 66 at which time the output of comparator 74 toggles to the binary "0" level and motor 20 is turned off.

A third embodiment of the exercising device 10" of the present invention is illustrated in FIG. 7. In this embodiment, a non-invasive blood flow detector 80 is coupled to the housing 16 of foot exercising device 10" by an electrical line 82. The non-invasive blood flow detector 80 is adapted to be placed around the leg of the patient and detects the blood flow in the patient's leg. Detector 80 generates an output signal on line 82 indicative of the blood flow in the patient's leg. While any appropriate blood flow detector 80 may be used, one suitable detector is a sonic detector manufactured by Metrix-Technics under the product designation Pulsed Doppler Ultrasonic Flow Detector.

The electrical line 82 is connected to a display unit 84 which is preferably, but not necessarily located at the top of housing 16. Display unit 84 provides the patient and/or the physician with a visual indication of the rate of blood flow through the patient's leg. This information is extremely important, since it will enable the physician to select both the pedal reciprocation frequency and the number of reciprocations during the passive mode of operation in a manner which is tailored to the specific needs of the patient being treated. It will also enable the patient to visually see that he is being helped by exercising device 10".

As noted above, the primary purpose of foot exercising device 10" is to prevent the formation of blood clots in the patients's legs. To this end, it is necessary to ensure that the blood flow through the patient's legs remains above some predetermined minimum value. In the preferred embodiment of the present invention, the display unit 84 includes an audible and/or visual alarm which is activated whenever the patient's blood flow falls below the predetermined level. Such an alarm may be formed by merely using a comparator circuit which compares the signal in line 82 (representative of the actual blood flow through the patient's legs) with a second signal (preferably adjustable by the physician) indicative of the minimum acceptable rate of blood flow. Whenever the actual blood flow falls below the minimum blood flow level, the comparator generates an output signal which can be applied to an audible alarm circuit.

In the embodiment illustrated in FIG. 7, both the display unit 84 and the alarm housed therein are connected to the housing 18. It is often desirable to locate both the display unit 84 and the associated alarm circuit at some central location such as the nurse's desk in a hospital ward. In such a case, the blood flow information generated by detector 80 will be transmitted to the central location either through cables or using radiowaves. If several foot exercising devices 10″ are used in the same ward, the signals from each of the different exercising devices 10″ may all be transmitted to the central location where they are displayed on associated displays 84. In the event that the blood flow through any of the patients' legs falls below the minimum acceptable value, an alarm signal will be generated at the central location indicating which patient is in danger.

In the embodiment of FIG. 7, the blood flow information is used merely for the purpose of displaying the instantaneous blood flow through the patient's legs and for generating an alarm signal whenever the blood flow falls below a predetermined minimum value. It is possible, however, to use the blood flow information as an additional control input for controlling the operation of foot exercising device 10″. A block diagram for such a device is illustrated in FIG. 8. This block diagram is identical to that of FIG. 2 with the addition of blood flow detector 80 and display and/or alarm circuit 84. The control circuit 28 may take the form of any of the control circuits illustrated in FIGS. 3, 4 or 6 or any other desirable variation thereon with the addition of the circuitry illustrated in FIG. 9. In this Figure, the block identified as counter circuit 86 represents the control circuit of the foregoing embodiments. By way of example, if the embodiment of FIG. 3 is utilized, counter circuit 86 includes elements 36-42. In such a case, counter circuit 86 would include a single output line (shown in solid lines) which is coupled to one input of OR-gate 88. If the control circuit of FIG. 6 is utilized, counter circuit 86 includes elements 36, 38 and 68-78. In such a case, counter circuit 86 includes both an on/off and a speed output. The on/off output is represented in solid lines and applied to one input of OR-gate 88 while the speed output is shown in dashed lines and would be applied to the speed control of motor 20 (in lieu of speed adjust switch 26).

In addition to counter circuit 86, control circuit 28″ includes a comparator 90 and a preset switch 92. The preset switch is preferably adjustable by the physician and generates an output signal indicative of the miniumum acceptable blood flow through the patient's legs. This signal is compared in comparator 90 to the output of blood flow detector 68. As long as the blood flow through the patient remains above the predetermined level set by preset switch 92, the output of comparator 90 will be a binary "0" and the on/off operation of motor 20 will be controlled by counter circuit 86 (i.e. as a function of the number of reciprocations of pedals 12, 14). If, at any time, the actual blood flow through the patient's legs falls below the preset value determined by preset switch 92, comparator 90 generates a binary "1" on its output and applies this signal to the on/off control of motor 20 via OR-gate 88. As a result, motor 20 will be turned on whenever the blood flow through the patient's legs falls below the predetermined minimum value. This is highly desirable since it ensures that the patient's legs will be exercised whenever his blood flow reaches a critical stage irrespective of the number of prior reciprocations of pedals 12, 14. While it is usually desirable to control the operation of motor 20 both as a function of the number of pedal reciprocations and the rate of blood flow through the patient's legs, it is sometimes desirable to control the operation of motor 20 solely as a function of the blood flow through the patient's legs. For example, it may be desirable to enable motor 20, and thereby place foot exercising device 10″ in a passive mode, whenever the blood flow through the patient falls below a predetermined level. In such cases, a bypass switch 94 (shown in phantom) may be added to control circuit 28″. Whenever it is desirable to control the operation of foot exercising device 10 solely as a function of the flow of blood through the patient, switch 94 is closed, thereby short-circuiting OR-gate 88 and connecting the output of comparator 90 directly to the on/off control of motor 20.

In the foregoing embodiment, the rate of blood flow through the patient's legs is used merely to control the on/off condition of motor 20. The speed of motor 20 may, however, also be controlled as a function of blood flow. In such a case, circuitry could be included to vary the speed of motor 20 as a linear or discrete function of the instantaneous blood flow through the patient. One example of a control circuit which varies the speed of motor 20 as a discrete function of blood flow is illustrated in FIG. 10. This circuitry is substantially identical to the speed control circuitry of FIG. 6 except that the output of blood flow detector 80, rather than the output of D/A converter 70, is applied to the inverting input terminal of comparator 72. Additionally, comparator 72 compares the output of blood flow detector 80 to a blood flow signal generated by a preset switch 96 which is adjustable by the physician and which indicates the blood flow level at which the reciprocating frequency is to change. Since the operation of speed adjust circuit 76 is otherwise identical to that described with reference to FIG. 6 above, and additional description of this circuit will not be set forth herein. The circuitry of FIG. 10 may be utilized either in lieu of or in connection with the circuitry of FIG. 9.

The present invention may be embodied in other specific forms without departing from the spirit or essential attributes thereof and, accordingly, reference should be made to the appended claims, rather than to the foregoing specification as indicating the scope of the invention.

What is claimed is:

1. A foot exercising device, comprising:
   a pair of foot pedals;
   motor means for reciprocating said foot pedals;
   blood flow detector means for detecting the flow of blood through a leg of a patient using said foot exercising device; and
   control means connected to said blood flow detector means for controlling the operation of said motor means as a function of said blood flow.

2. The foot exercising device of claim 1, wherein said control means causes said motor means to vary the reciprocation frequency of said pedals as a function of said blood flow.

3. The foot exercising device of claim 1, wherein said control means enables said motor means whenever said blood flow falls below a predetermined value.

* * * * *